US007419263B1

(12) United States Patent
Pearce et al.

(10) Patent No.: US 7,419,263 B1
(45) Date of Patent: Sep. 2, 2008

(54) DEVICE AND METHOD FOR ASSISTING DEVELOPMENT OF AN INFANT'S VISUAL ACUITY AND FOR TRANSFERRING A MOTHER'S SCENT TO AN INFANTILE ENVIRONMENT

(75) Inventors: Kenneth F. Pearce, Danville, KY (US); Andrea W. Mesplay, Danville, KY (US)

(73) Assignee: Mobile Mom, LLC, Harrodsburg, KY (US)

( * ) Notice: Subject to any disclaimer, the term of this patent is extended or adjusted under 35 U.S.C. 154(b) by 471 days.

(21) Appl. No.: 11/167,674

(22) Filed: Jun. 27, 2005

(51) Int. Cl.
*A61B 3/00* (2006.01)

(52) U.S. Cl. ....................... 351/203; 351/239; 351/246; 442/96

(58) Field of Classification Search ................. 351/203, 351/239, 246; 450/1; D21/476; 442/59, 442/96; 428/905
See application file for complete search history.

(56) References Cited

U.S. PATENT DOCUMENTS

| | | | | |
|---|---|---|---|---|
| 1,669,061 | A | 5/1928 | Meltzer | |
| 2,522,381 | A | 9/1950 | Kramer | |
| 3,065,944 | A | 11/1962 | Libendorfer | |
| 3,570,139 | A | 3/1971 | Ladd et al. | |
| 4,283,011 | A | 8/1981 | Spector | |
| 4,514,995 | A | 5/1985 | Curtis | |
| 4,582,492 | A | 4/1986 | Etter et al. | |
| 4,631,754 | A | 12/1986 | Ryan | |
| 4,724,623 | A | 2/1988 | Silverman | |
| 4,989,285 | A | 2/1991 | Troncone et al. | |
| 5,052,057 | A | 10/1991 | Fetner | |
| 5,423,711 | A | 6/1995 | Dorland | |
| 5,813,866 | A | 9/1998 | Maeda | |
| 6,112,749 | A | 9/2000 | Hall et al. | |
| 6,247,178 | B1 | 6/2001 | Bilda | |
| 6,626,536 | B2 * | 9/2003 | Mesplay | 351/203 |
| 6,772,891 | B1 | 8/2004 | Song | |
| 2002/0006455 | A1 | 1/2002 | Levine | |

OTHER PUBLICATIONS

The Enfamil® Family of Formulas™ Baby Book © 1997, Mead Johnson & Company.

* cited by examiner

*Primary Examiner*—Ricky Mack
*Assistant Examiner*—James R Greece
(74) *Attorney, Agent, or Firm*—Kenneth F. Pearce

(57) ABSTRACT

A device for assisting the development of an infant's visual acuity and for transferring the mother's scent to an infantile environment. Supple fabric contacts an area of the mother's body for absorbing a portion of the mother's scent and is thereafter transferred and located in proximity with the infantile environment for venting the transferred scent about the infantile environment. Due to the device's contrasting colors, the training of the infant's visual acuity can be enhanced.

22 Claims, 4 Drawing Sheets

FIG 15

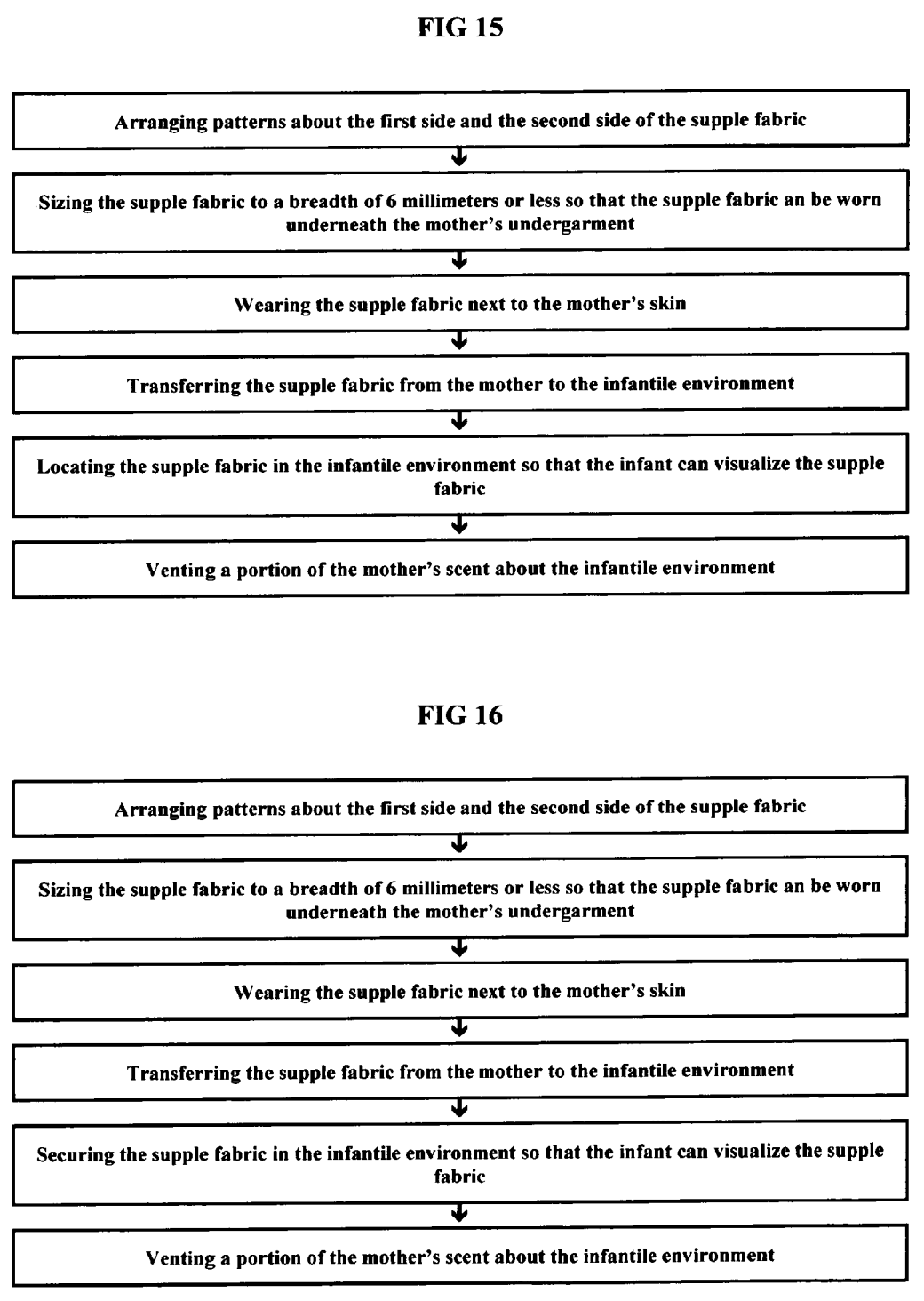

Arranging patterns about the first side and the second side of the supple fabric

↓

Sizing the supple fabric to a breadth of 6 millimeters or less so that the supple fabric an be worn underneath the mother's undergarment

↓

Wearing the supple fabric next to the mother's skin

↓

Transferring the supple fabric from the mother to the infantile environment

↓

Locating the supple fabric in the infantile environment so that the infant can visualize the supple fabric

↓

Venting a portion of the mother's scent about the infantile environment

FIG 16

Arranging patterns about the first side and the second side of the supple fabric

↓

Sizing the supple fabric to a breadth of 6 millimeters or less so that the supple fabric an be worn underneath the mother's undergarment

↓

Wearing the supple fabric next to the mother's skin

↓

Transferring the supple fabric from the mother to the infantile environment

↓

Securing the supple fabric in the infantile environment so that the infant can visualize the supple fabric

↓

Venting a portion of the mother's scent about the infantile environment

FIG 17

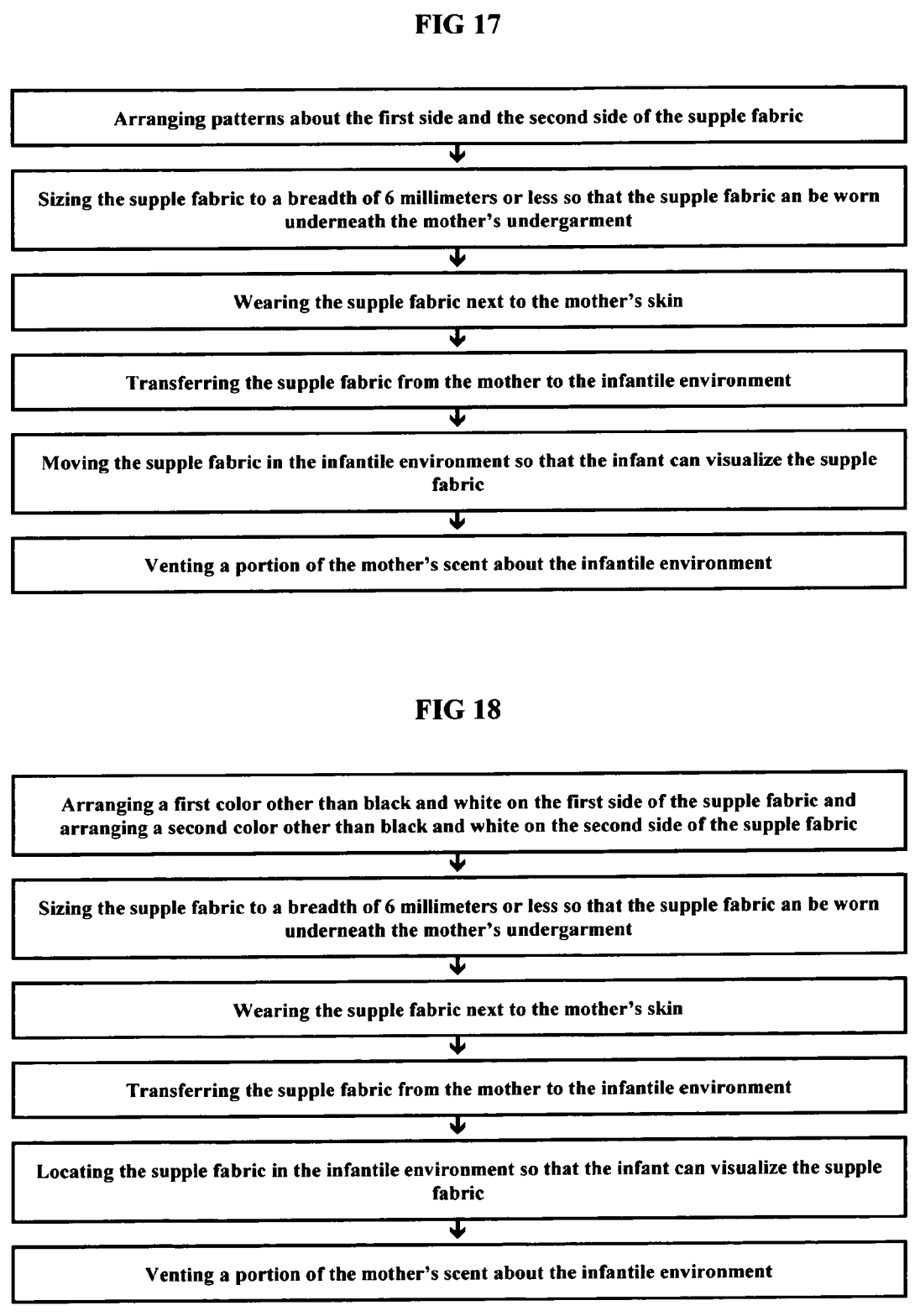

Arranging patterns about the first side and the second side of the supple fabric

↓

Sizing the supple fabric to a breadth of 6 millimeters or less so that the supple fabric an be worn underneath the mother's undergarment

↓

Wearing the supple fabric next to the mother's skin

↓

Transferring the supple fabric from the mother to the infantile environment

↓

Moving the supple fabric in the infantile environment so that the infant can visualize the supple fabric

↓

Venting a portion of the mother's scent about the infantile environment

FIG 18

Arranging a first color other than black and white on the first side of the supple fabric and arranging a second color other than black and white on the second side of the supple fabric

↓

Sizing the supple fabric to a breadth of 6 millimeters or less so that the supple fabric an be worn underneath the mother's undergarment

↓

Wearing the supple fabric next to the mother's skin

↓

Transferring the supple fabric from the mother to the infantile environment

↓

Locating the supple fabric in the infantile environment so that the infant can visualize the supple fabric

↓

Venting a portion of the mother's scent about the infantile environment

DEVICE AND METHOD FOR ASSISTING DEVELOPMENT OF AN INFANT'S VISUAL ACUITY AND FOR TRANSFERRING A MOTHER'S SCENT TO AN INFANTILE ENVIRONMENT

BACKGROUND OF THE INVENTION

1. Field of the Invention

In the most general sense, the present invention relates to devices that can be assimilated with an infantile environment. An infantile environment can include such objects as incubators, cradles, cribs or bassinets. The invention is useful in hospital wards for newborns and premature babies as well as day care facilities. Due to the device's contrasting colors, the training or stimulation of the infant's visual acuity can be enhanced. In conjunction with the contrasting colors, fabrics or other supple materials which can absorb and thereafter transfer a portion of the scent of the infant's mother to a location apart from the mother create another attribute of the invention. When the device is assimilated into the infantile environment, the mother's scent is vented about the infant's environment such that the infant's olfactory senses can be stimulated by the mother's scent without the mother being present.

2. Description of the Previous Art a) U.S. Pat. No. 5,423,711—Dorland enables a convertible body garment with odor absorbing properties and process of using the convertible body garment. The Dorland garment is formed from a rectangular piece of fabric (16) which may be made from naturally occurring materials or blends thereof, such as cotton and/or blends with man made materials which absorb perspiration or body secretions. A pair of removable straps (18) are attached to the elongated side (20) of the rectangular shaped garment. Pockets (32) are attached to the inner surface of the garment in proximity to the breasts or axillae. The pockets are defined by a loose weave designed to retain body order absorbing material. After the mother's body odor has been absorbed, the garment (10) is attached to a crib's mattress (50). In another embodiment, the '711 garment is attached to an infant seat, carrier or swing. And Column 4, lines 23-44, teach, "In a preferred application of the invention, the use of body odor absorbing materials attached to the inner surface of the garment enhances the absorbency of odor . . . . A process of promoting bonding between a person and an infant in accordance with the invention includes wearing a garment in contact with at least the person's body, such as the torso, comprising a material which absorbs odor from the body and a fastening means for attaching the garment to the body for a time sufficient to retain the odor; and attaching the worn garment to a garment support with fastening means sufficiently close to the infant so that the infant may smell the retained odor for a time sufficient to promote bonding." By reference, the disclosure of the Dorland patent is specifically incorporated into the current Application, and more particularly, the disclosure therein related to odor absorbing materials and the resultant olfactory bonding between infants and their mothers.

2) U.S. Pat. No. 6,112,749—Hall, et. al., discloses the use of an absorbent pad made of cotton, felt, paper, etc. that has been impregnated with an odor, preferably vanilla, that is pleasing to the infant. Application of moisture activates the odor dot on the baby bottle. In another embodiment, an odor ring rather than a dot is affixed to the baby bottle. The '749 device also enables a methods inducing greater consumption of liquids, as well as, enriching the olfactory environment of the bottle's user.

3) U.S. Pat. No. 4,283,011—Spector enables a scented sticker that can be applied to clothing. The Spector stickers are embedded with a volatile having the odor analogous to the shape of the sticker.

4) U.S. Pat. No. 4,989,285—Troncone, et. al., teaches a security blanket, preferably 35 centimeters by 45 centimeters, constructed to feel like the amnion lining in which the baby resides before birth. The Troncone blanket has one side that is soft brushed flannel and a second side made of charmeuse satin.

5) U.S. Pat. No. 4,582,492—Etter, et. al., enables a behavioral modification method using microencapsulation of odors on a patch. Dominant and subservient odors are microencapsulated onto disks. When the subject's urge becomes so strong that he feels as if he is loosing control, the disk is scratched which releases the subservient odor. After a period of time, the subservient odor fades and the dominant pleasant odor becomes pervasive once again and the subject is rewarded for avoiding the bad habit.

6) U.S. Pat. No. 5,813,866—Maeda describes a bed sheet or a lap robe including a cloth chart for learning characters. A plurality of pieces and kinds of cloth in color are connected in a continuous manner along the circumference of the face of the learning chart so that beautiful feelings for infants and children are formed. Pieces (41), (42), (43), (44) and (45) are respectively red, green, yellow, brown and blue.

7) U.S. Pat. No. 3,570,139—Ladd, et. al., enables an instructional apparatus for use in early child development. The Ladd book includes visual and chemical-odor producing stimuli that allow the child to associate the thing displayed with its aroma. The display sheets (28) include incentive means (14) that are integrated with the story line as well as illustrative material to encourage the student to operate the Ladd, et. al., apparatus. For example, the '139 Patent teaches that the candy canes exemplified therein also smell like peppermint.

8) U.S. Pat. No. 5,199,842—Watt et. al., describes a nursing scarf and enables a method of nursing an infant utilizing the scarf.

9) U.S. Pat. No. 6,247,178—Bilda enables a convertible, scent retaining garment blanket. Bilda utilizes a shirt with detachable sleeves. To practice of the '178 detachable shirt, the parent wears the shirt and then detaches the sleeves from the body of the shirt. Either one of the sleeves or the torso of the shirt is used as a baby blanket.

10) US Published Patent Application No. 20020006455 A1—Levine describes a baby food selection and method. Levine utilizes scratch and sniff technology to incorporate food flavor and food odors onto food containers, cards, game pieces or toys. By smelling or tasting the flavor or scent imparted to the food containers, cards, game pieces or toys, the pre-speaking baby can indicate the preferred food.

11) U.S. Pat. No. 6,626,536 B2—Mesplay enables a device and method for assisting development of an infant's visual acuity and for transferring a mother's scent to an infantile environment. The Mesplay Description of the Preferred Embodiments, in part, reads:

> FIG. 1 depicts a black side (32) of supple fabric (30) including an aperture (34) that can be hooked onto a projection of an infantile environment (not shown), thereby attaching supple fabric (30) to the infantile environment. FIG. 2 discloses a neutral white side (38) of supple fabric (30) and aperture (34). FIG. 3 portrays device (30) where aperture (34) has received thread (42). However, those skilled in the art recognize that thread (42) can be sewn directly into supple fabric (30), thereby circumventing use of aperture (34). FIG. 4 exemplifies, device (30) suspended from canopy (44) of bassinet (40) by thread (42). In FIGS. 5-8, linear (FIG. 5) and other geometric black on white patterns (FIG. 6, polka dot; FIG. 7, rectangular or square; FIG. 8, triangular) are depicted. Importantly, those skilled in the art recognized the patterns could just as easily be white on black backgrounds. Moreover, practice of the present invention is not limited to patterns disclosed in FIGS. 5-8, but can easily accommodate other geometric patterns. And still in accordance with the present invention, the sides (not shown) opposite the geometric pattern sides (50, 52, 54 and 56) of supple fabric (30) are neutral, i.e., white, off-white, pastel beige, pastel yellow, pastel gray, pastel blue, pastel pink, to name a few of the plethora of neutral colors available for use. Additionally, opposite sides (not shown) can be composed of a backing separate from supple fabric (30), or it can be composed solely of supple fabric (30).

The '536 patent appears to enable supple fabrics that have either a solid black side and a solid neutral or white side or a geometric black and white pattern on a first side of the fabric and a neutral solid colored second side. In accordance with Mesplay, the colors of the neutral side can be either white, off-white, pastel beige, pastel yellow, pastel gray, pastel blue or pastel pink. Mesplay appears to be silent regarding the use of black and white patterns on both sides of the fabric, a black and white pattern on a first side of the device and a pattern of other colors on the second side of the device or colors other than black and white utilized on each side of the '536 device.

9) The Enfamil® Family of Formulas™ Baby Book© 1997, Mead Johnson & Company. The Mead Johnson soft plastic Baby Book teaches, "... black and white patterns are easier for babies to distinguish than colors. While they can see colors, the sharp contrast of black and white holds their attention for longer periods of time." And the soft plastic Baby Book features pages of black patterns on white backgrounds.

SUMMARY OF THE INVENTION

The present device and method of using the device are directed toward assisting or stimulating the developments of the infant's visual acuity and for transferring the mother's scent to an infantile environment. Infantile environments, include but are not limited to incubators, cradles, infants' car seats, cribs or bassinets. The present invention can be practiced in hospital, home and/or daycare-type surroundings.

Supple fabrics, such as, cottons, silks, or manmade blends that can absorb the scent of the mother are incorporated into the invention. Since the practice of certain embodiments of the present invention require the mother to wear the device next to the mother's skin, the supple fabrics are manufactured to feel smooth and soft to the mother's skin. The current device absorbs the mother's scent when placed in proximity with the mother's skin, and generally, the mother will wear the apparatus inside an undergarment to absorb the mother's scent. Based on experimental testing, it has been determined that mothers frequently find insertion of the apparatus into the cup of the brassier provides for adequate absorption of the mother's scent as well as ease of use.

Supple fabrics used to practice the present invention have a breadth of no greater than 10 millimeters, preferably 1-6 millimeters, and will adequately absorb a transferable portion of the mother's scent, after a relatively short exposure to the mother's skin. Before assimilating the apparatus into the infantile environment, the mother can wear the device for about three hours; however, the current invention is also functional, if the it is placed next to the mother's skin for more or for less than three hours. To lessen the any potential occurrence of fabric bulking, devices practiced in accordance with select embodiments of the present invention have a perimeter of 75 centimeters or less.

After the current invention has been entered into the infantile environment, the infant can visualize the highly contrasted colors of the device as well as be exposed to the mother's scent, when the mother is absent. Representative contrasted colors for embodiments of the present invention can include:

black and white patterns on the first side and the second side of the device;

black and white patterns on the first side of the device and patterns having colors other than black on the second side of the device;

patterns of colors other than black on the first side of the device and a neutral color on the second side of the device;

patterns of colors other than black on the first side of the device and patterns of colors other than black on the second side of the device;

patterns of colors other than black and white on the first side of the device and patterns of colors other than black and white on the second side of the device;

black and white patterns on the first side of the device and patterns having colors other than white on the second side of the device;

patterns of colors other than white on the first side of the device and a neutral color on the second side of the device; or patterns of colors other than white on the first side of the device and patterns of colors other than white on the second side of the device.

Another representative pattern of the present invention includes fabric having a first side color other than black or white and a second side color other than black or white. Neutral colors of the present invention can include, among other colors, solid white, solid off-white, solid pastel beige, solid pastel yellow, solid pastel gray, solid pastel blue or solid pastel pink. Depending on preselected engineering parameters, select embodiments of the current invention can be manufactured with a backing to create the second side of the device. In still other embodiments, a single supple fabric, without a backing, creates the first and second sides of the current invention.

An aspect the present invention is to provide a device assisting with the development of an infant's visual acuity and for transferring the mother's scent to an infantile environment.

It is another aspect of the present invention to enable a method for assisting the development of the infant's visual acuity and for transferring the mother's scent to the infantile environment.

Still another aspect of the present invention is to provide a device including highly contrasted patterns for stimulating the infant's visual acuity.

Yet another aspect of the present invention is to provide embodiments including highly contrasted geometric patterns for stimulating the infant's visual acuity.

Still another aspect of the present invention is to provide embodiments having a supple fabric for absorbing a portion of the mother's scent to be transferred to the infantile environment.

It is yet another aspect of the present invention to provide embodiments featuring highly contrasted patterns utilizing colors other than white.

Yet another aspect of the present invention to provide embodiments featuring highly contrasted patterns utilizing colors other than black.

Still another aspect of the present invention is to provide embodiments featuring a black and white pattern on a first side of the device and a black and white pattern on the second side of the device.

An embodiment of the present invention can be described as a device for assisting development of an infant's visual acuity and for transferring a mother's scent to an infantile environment, comprising: an assimilator for assimilating the device into the infantile environment; and a supple fabric for assisting development of the infant's visual acuity, wherein the supple fabric further comprises one of the following combinations of patterns for a first side and a second side of the device; the combinations comprising: i) black and white on the first side and black and white on the second side; ii) black and white on the first side and colors other than black on the second side; iii) colors other than black on the first side and a neutral color on the second side; iv) colors other than black on the first side and colors other than black on the second side; v) colors other than black and white on the first side and colors other than black and white on the second side; vi) black and white on the first side and colors other than white on the second side; vii) colors other than white on the first side and a neutral color on the second side; or viii) colors other than white on the first side and colors other than white on the second side.

Another embodiment of the present invention can be described as a method for assisting development of infant's visual acuity and for transferring a scent of a mother to an infantile environment, comprising the steps of: arranging patterns about a first side and a second side of a supple fabric, wherein said patterns comprise one of the following combinations: i) black and white on the first side and black and white on the second side; ii) black and white on the first side and colors other than black on the second side; iii) colors other than black on the first side and a neutral color on the second side; iv) colors other than black on the first side and colors other than black on the second side; v) colors other than black and white on the first side and colors other than black and white on the second side; vi) black and white on the first side and colors other than white on the second side; vii) colors other than white on the first side and a neutral color on the second side; or viii) colors other than white on the first side and colors other than white on the second side; sizing the supple fabric such that the supple fabric includes a breadth of 6 millimeters or less and can be worn underneath a mother's undergarment; wearing the supple fabric next to the mother's skin; transferring the supple fabric from the mother to the infantile environment; locating the supple fabric about the infantile environment such that the infant can visualize the supple fabric; and venting a portion of the mother's scent about the infantile environment.

Yet another embodiment of the present device can be described as a device for assisting development of an infant's visual acuity and for transferring a mother's scent to an infantile environment, comprising: means for assimilating the device into the infantile environment; and a supple fabric, including a backing, sized for contacting the mother's skin underneath an undergarment for absorbing a portion of the mother's scent and for assisting development of the infant's visual acuity, wherein the supple fabric further comprises one of the following combinations of patterns for a first side and a second side of the device; the combinations comprising: i) black and white on the first side and black and white on the second side; ii) black and white on the first side and colors other than black on the second side; iii) colors other than black on the first side and a neutral color on the second side; iv) colors other than black on the first side and colors other than black on the second side; v) colors other than black and white on the first side and colors other than black and white on the second side; vi) black and white on the first side and colors other than white on the second side; vii) colors other than white on the first side and a neutral color on the second side; or viii) colors other than white on the first side and colors other than white on the second side.

Yet still another embodiment of the present invention can be described as a device for assisting development of an infant's visual acuity and for transferring a mother's scent to an infantile environment, comprising: means for assimilating the device into said infantile environment; and a supple fabric sized for contacting the mother's skin underneath an undergarment for absorbing the mother's scent and for assisting development of the infant's visual acuity, wherein the supple fabric further comprises a first side having a first color other than black or white and a second side having a second color other than black or white.

It is the novel and unique interaction of these simple elements which creates the methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 15 is an illustration of the steps of an embodiment of the present method.

FIG. 16 is a depiction of the steps of another embodiment of the present invention.

FIG. 17 is an exemplification of the steps of yet another embodiment of the current method.

FIG. 18 is an illustration of the steps of yet another embodiment of the current method.

DESCRIPTION OF THE PREFERRED EMBODIMENTS

Although the disclosure hereof is detailed to enable those skilled in the art to practice the invention, the embodiments published herein merely exemplify the present invention.

Figure 1:
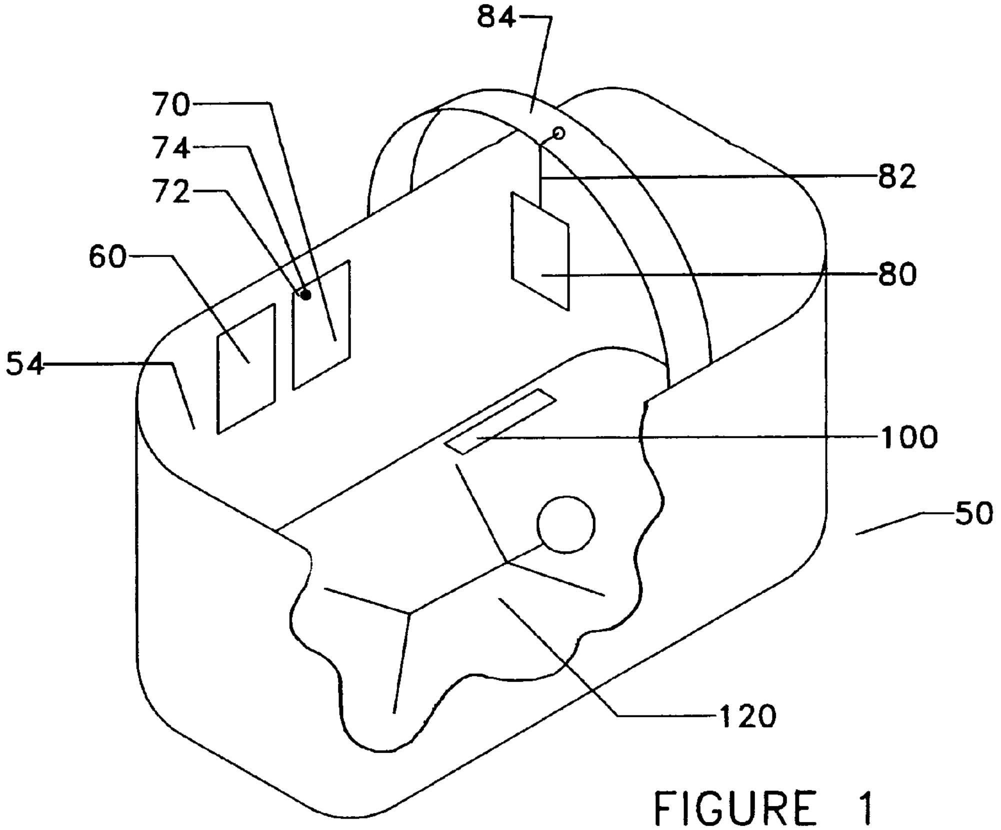
FIG. 1 is a view of an infantile environment, within the scope of the present invention.
Figure 2:
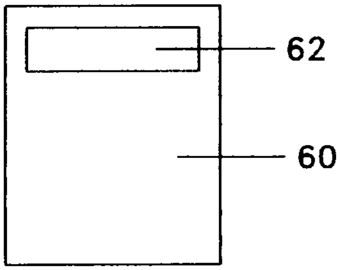
FIG. 2 is a view of a supple fabric and an adhesive, within the scope of the present invention.

FIG. 1 portrays an infantile environment (50), such as incubators, cradles, infants' car seats, cribs, bassinets or the like and ways for assimilating the current invention into infantile environment (50). FIG. 2 shows supple fabric (60) including an adhesive (62) for securing supple fabric (60) to infantile environment (50). Assimilator (62) can be a peeland-stick adhesive, adhesive tape or another type of adhesive that allows supple fabric (60) to be temporarily adhered to infantile environment (50).

Figure 3:
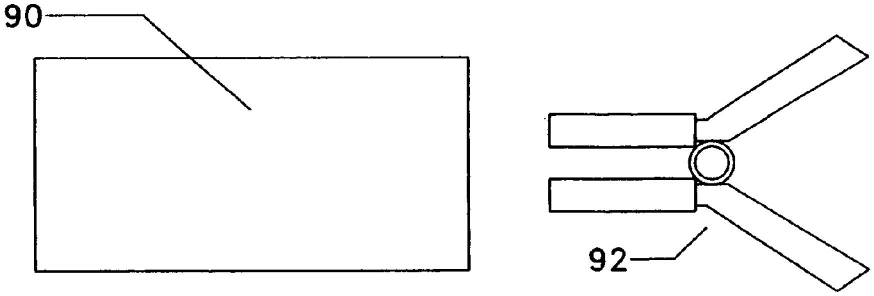
FIG. 3 portrays an assimilator for assimilating a supple fabric into an to infantile environment, within the scope of the present invention.
Figure 6:
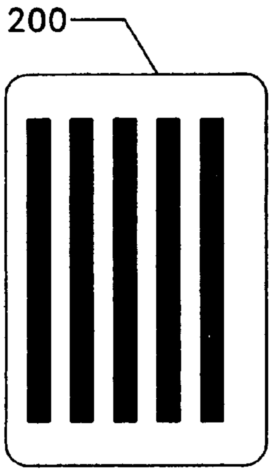
FIGS. 6, 7, 8, 9, 10, 11 and 12 are frontal views of patterns, within the scope of the present invention.
Figure 7:
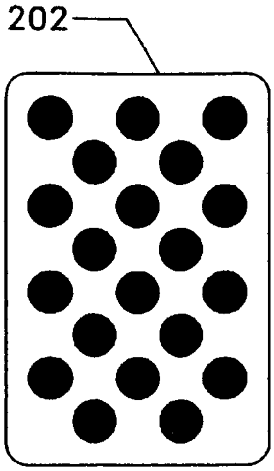
Figure 8:
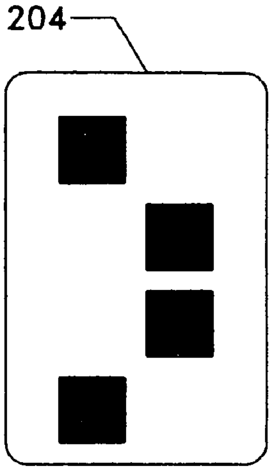
Figure 9:
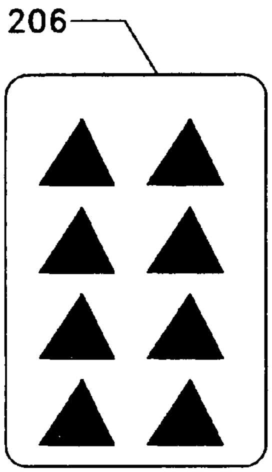
Figure 10:
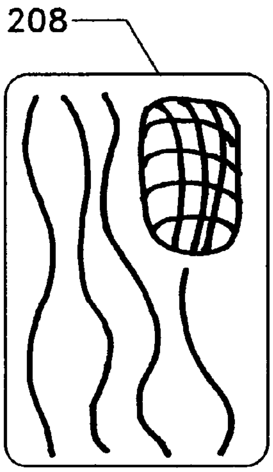
Figure 11:
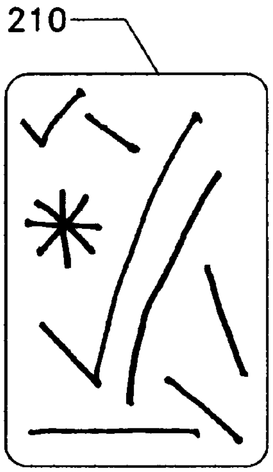
Figure 12:
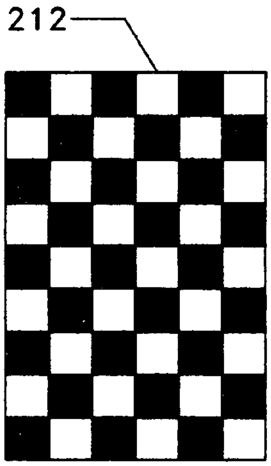

Returning to FIG. 1, assimilator or aperture (72) engages projection (74) of infantile environment (50) to support supple fabric (70) along a wall (54) of infantile environment (50). Assimilator or suspender (82) depending from holder (84) supports supple fabric (80) about infantile environment (50) while also allowing supple fabric (80) to move about infantile environment (50). FIG. 3 depicts a clip (92) for assimilating supple fabric (90) to infantile environment (50). As shown in FIG. 1, supple fabric (100) is laid in infantile environment, thereby assimilating supple fabric (100) into infantile environment (50).

The enablements disclosed in FIGS. 1-5 regarding assimilation of supple fabrics (60), (70), (80), (90) or (100) into an infantile environment are by way illustration and not limitation. In other words, those skilled in the art recognize there are other ways to assimilate a supple fabric into an infantile environment.

Supple fabrics (60), (70), (80), (90) and (100) are composed of cotton, silk or manmade blends that will absorb a portion of the mother's scent. However, it has been determined that various blends of cottons yield better absorption and transference of the mother's scent per square centimeter of fabric. In accordance with the present invention, supple fabrics are soft to the touch and nonirritating to the skin—allowing the mother to wear the supple fabric underneath her undergarments for prolonged periods of time of twelve to twenty-four hours or more. It is suggested that the mother contact her skin with the current invention for about three hours to absorb a portion of the mother's scent that can thereafter be transferred to the infantile environment. However, supple fabrics of the current invention need only contact the mother's skin for a few minutes to be able to absorb a portion of the mother's scent that can be transferred to the infantile environment.

Figure 4:
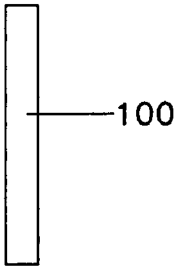
FIG. 4 is a side view of an embodiment of a supple fabric, within the scope of the present invention.
Figure 5:
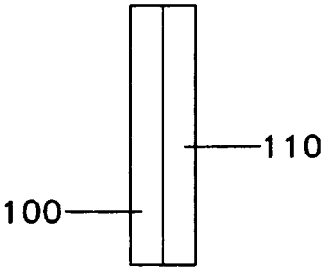
FIG. 5 is a side view of another embodiment of a supple fabric, within the scope of the present invention.

FIG. 4 represents a side view of supple fabric (100), within the scope of the present invention, without a backing. Supple fabric (100) can have a breadth of from about 1 millimeter to about 6 millimeters. FIG. 5 depicts a side view of supple fabric (100), within the ambit of the current invention, having a backing (110). Supple fabric (100) and backing (110) can have a breath of from about 1 millimeter to about 10 millimeters. Backings of the current invention can be the same material as supple fabric (100) or of a material different than supple fabric (100). With reference to FIGS. 1-5, supple fabrics (60), (70), (80), (90) or (100) can have a perimeter of 75 centimeters or less.

By way of illustration and not limitation, as shown in FIGS. 6-12, in accordance with the present invention, any of the supple fabrics (60), (70), (80), (90) or (100) portrayed in FIGS. 1-5 can support one of the patterns (200), (202), (204), (206), (208), (210) or (212). Examples of contrasted colors for the patterns (200), (202), (204), (206), (208), (210) and (212) of the present invention can include: black and white patterns on the first side and the second side of the device; black and white patterns on the first side of the device and patterns having colors other than black on the second side of the device; patterns of colors other than black on the first side of the device and a neutral color on the second side of the device; patterns of colors other than black on the first side of the device and patterns of colors other than black on the second side of the device; patterns of colors other than black and white on the first side of the device and patterns of colors other than black and white on the second side of the device; black and white patterns on the first side of the device and patterns having colors other than white on the second side of the device; patterns of colors other than white on the first side of the device and a neutral color on the second side of the device; or patterns of colors other than white on the first side of the device and patterns of colors other than white on the second side of the device. Patterns of the current invention can be either geometric or freehand. Neutral colors of the present invention can include white, off-white, pastel beige, pastel yellow, pastel gray, pastel blue, pastel pink, to name a few of the plethora of neutral colors available for use.

Figure 13:
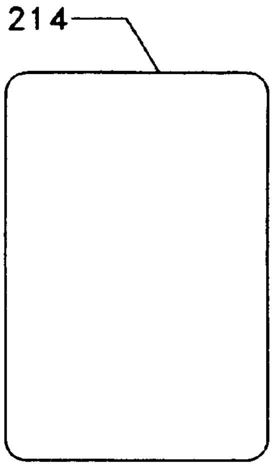
FIG. 13 is a plan view of a first side of an embodiment, within the scope of the present invention.
Figure 14:
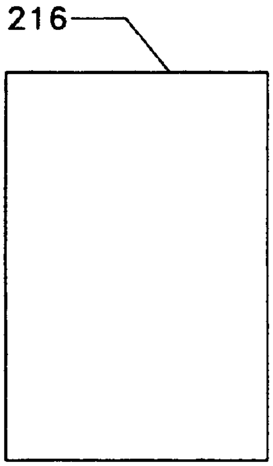
FIG. 14 is a plan view of a second side of the FIG. 13 embodiment, within the scope of the present invention.

In accordance with the present invention, as shown in FIGS. 13 and 14, any of the supple fabrics (60), (70), (80), (90) or (100) can include first side (214) having a first color other than black or white and a second side (216) having a second color other than black or white. Steps associated with the methods of practicing the present invention are depicted in FIGS. 15-17.

Regarding the embodiments disclosed herein, locating or assimilating the supple fabrics or devices in proximity to the infantile environment vents the mother's scent about the infantile environment while also exposing the infant to the contrasted patterns is believed to assist in the development of the infant's visual acuity. In accordance with the present invention, both the infant's visual and olfactory senses are stimulated.

Having disclosed the invention as required by Title 35 of the United States Code, Applicants now pray respectfully that Letters Patent be granted for their invention in accordance with the scope of the claims appended hereto.

What is claimed is:

1. A device for assisting development of an infant's visual acuity and for transferring a mother's scent to an infantile environment, comprising:

a) an assimilator for assimilating said device into said infantile environment; and b) a supple fabric sized for contacting said mother's skin underneath an undergarment for absorbing said mother's scent and for assisting development of said infant's visual acuity, wherein said supple fabric further comprises one of the following combinations of patterns for a first side and a second side of said device; said combinations comprising:

i) black and white on said first side and black and white on said second side;

ii) black and white on said first side and a plurality of colors other than black on said second side;

iii) a plurality of colors other than black on said first side and a neutral color on said second side;

iv) a plurality of colors other than black on said first side and colors other than black on said second side;

v) a plurality of colors other than black on said first side and a plurality of colors other than white on said second side;

vi) black and white on said first side and a plurality of colors other than white on said second side;

vii) a plurality of colors other than white on said first side and a neutral color on said second side; or viii) a plurality of colors other than white on said first side and a plurality of colors other than white on said second side.

2. The invention of claim 1, wherein said supple fabric comprises a breadth of 6 millimeters or less.

3. The invention of claim 2, wherein said patterns are geometric.

4. The invention of claim 2, wherein said assimilator is a suspender.

5. The invention of claim 2, wherein said assimilator is an aperture.

6. The invention of claim 2, wherein said assimilator is an adhesive.

7. The invention of claim 3 further comprising a backing.

8. A method for assisting development of infant's visual acuity and for transferring a scent of a mother to an infantile environment, comprising the steps of:

a) arranging patterns about a first side and a second side of a supple fabric, wherein said patterns comprise one of the following combinations for said first side and said second side of said supple fabric; said combinations comprising:

i) black and white on said first side and black and white on said second side;

ii) black and white on said first side and a plurality of colors other than black on said second side;

iii) a plurality of colors other than black on said first side and a neutral color on said second side;

iv) a plurality of colors other than black on said first side and colors other than black on said second side;

v) a plurality of colors other than black on said first side and a plurality of colors other than white on said second side;

vi) black and white on said first side and a plurality of colors other than white on said second side;

vii) a plurality of colors other than white on said first side and a neutral color on said second side; or viii) a plurality of colors other than white on said first side and a plurality of colors other than white on said second side;

b) sizing said supple fabric such that said supple fabric includes a breadth of 6 millimeters or less and can be worn underneath a mother's undergarment;

c) wearing said supple fabric next to said mother's skin;

d) transferring said supple fabric from said mother to said infantile environment; and e) locating said supple fabric about said infantile environment so that said infant can visualize said supple fabric as a portion of said mother's scent is vented about infantile environment.

9. The method of claim 8 further comprising the step of securing said supple fabric about said infantile environment.

10. The method of claim 8 further comprising the step of allowing said supple fabric to move about said infantile environment.

11. The method of claim 8, wherein said step of wearing said supple fabric next to said mother's skin is for at least three hours.

12. A device for assisting development of an infant's visual acuity and for transferring a mother's scent to an infantile environment, comprising:

a) means for assimilating said device into said infantile environment; and b) a supple fabric, including a backing, sized for contacting said mother's skin underneath an undergarment for absorbing a portion of said mother's scent and for assisting development of said infant's visual acuity, wherein said supple fabric further comprises one of the following combinations of patterns for a first side and a second side of said device; said combinations comprising:

i) black and white on said first side and black and white on said second side;

ii) black and white on said first side and a plurality of colors other than black on said second side;

iii) a plurality of colors other than black on said first side and a neutral color on said second side;

iv) a plurality of colors other than black on said first side and colors other than black on said second side;

v) a plurality of colors other than black on said first side and a plurality of colors other than white on said second side;

vi) black and white on said first side and a plurality of colors other than white on said second side;

vii) a plurality of colors other than white on said first side and a neutral color on said second side; or viii) a plurality of colors other than white on said first side and a plurality of colors other than white on said second side.

13. The invention of claim 12, wherein said supple fabric comprises a breadth of 6 millimeters or less.

14. The invention of claim 12, wherein said patterns are geometric.

15. The invention of claim 12, wherein said means for assimilating is a suspender.

16. The invention of claim 12, wherein said means for assimilating is an aperture.

17. The invention of claim 12, wherein said means for assimilating is an adhesive.

18. The invention of claim 13, wherein said supple fabric is cotton.

19. A device for assisting development of an infant's visual acuity and for transferring a mother's scent to an infantile environment, comprising:

a) means for assimilating said device into said infantile environment; and b) a supple fabric sized for contacting said mother's skin underneath an undergarment for absorbing said mother's scent and for assisting development of said infant's visual acuity, wherein said supple fabric further comprises a first side having a first color other than black or white and a second side having a second color other than black or white.

20. The invention of claim 19, wherein said means for assimilating is a suspender.

21. The invention of claim 19, wherein said means for assimilating is an aperture.

22. The invention of claim 19, wherein said means for assimilating is an adhesive.

* * * * *